United States Patent [19]

Matyus et al.

[11] Patent Number: 5,705,529
[45] Date of Patent: Jan. 6, 1998

[54] N-BENZOYL AMINO ACID DERIVATIVES PHARMACEUTICAL COMPOSITIONS CONTAINING THEM AND PROCESS FOR PREPARING SAME

[75] Inventors: Peter Matyus; Erzsebet Zara; Lajos Farkas; Agnes Papp; Antal Simay; Lajos Toldy; Ferenc Andrasi; Katalin Goldschmidt; Eszter Hodula; Ildiko Mathe; Klara Sutka; Zsuzsanna Fittler; Valeria Vitkoczi; Laszlo Sebestyen; Istvan Sziraki; Marta Rusz; Eva Gal, all of Budapest, Hungary

[73] Assignee: Gyogyszerkutato Intezet KFT, Budapest, Hong Kong

[21] Appl. No.: 540,924

[22] Filed: Oct. 11, 1995

Related U.S. Application Data

[63] Continuation of Ser. No. 85,003, Jun. 29, 1993.

[30] Foreign Application Priority Data

Jun. 30, 1992 [HU] Hungary .................. P9202172

[51] Int. Cl.[6] .................. A61K 31/215; C07C 229/14
[52] U.S. Cl. .................. 514/541; 514/616; 514/617; 560/41; 562/508; 564/155
[58] Field of Search .................. 514/541, 616, 514/617; 564/155; 560/41; 562/508

[56] References Cited

U.S. PATENT DOCUMENTS

| 4,515,920 | 5/1985 | Erickson | 525/54.11 |
| 4,904,680 | 2/1990 | Matsui et al. | 564/155 |

FOREIGN PATENT DOCUMENTS

| 0011845 | 6/1980 | European Pat. Off. | |
| 0051828 | 5/1982 | European Pat. Off. | |
| 59108 | 9/1982 | European Pat. Off. | |
| 173441 | 3/1986 | European Pat. Off. | |
| 0393355 | 1/1960 | Sweden | 564/155 |
| 858426 | 1/1961 | United Kingdom | |

OTHER PUBLICATIONS

Journal of Org. Chem., 46, pp. 4524–4529 (1981) Bergeron, R.J. et al, "Flexible Synthesis of Polyamine Catecholamides".

Primary Examiner—Yogendra N. Gupta
Attorney, Agent, or Firm—Michael N. Meller

[57] ABSTRACT

The invention relates to novel N-benzoylamino acid derivatives of the general formula (I),

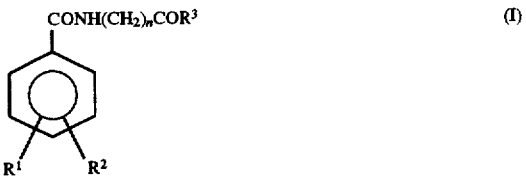

wherein
$R^1$ and $R^2$, which are the same or different, stand for a hydroxyl group optionally bearing an acetyl group; or a $C_{1-6}$alkoxy group optionally substituted by a phenyl group;
n means an integer from 2 to 15
as well as their tautomers, racemates and optically active individual (pure) isomers or mixtures thereof and the salts of these compounds and pharmaceutical compositions containing these compounds.

The invention relates also to a process for the preparation of compounds of the general formula (I).

The compounds of general formula (I) inhibit the peroxidation of lipids and therefore, they are expected to be useful for the treatment of diseases being in an indirect or direct connection with pathological oxidation processes, chiefly for the treatment and/or prevention of ischaemic and reperfusion tissue injuries, inflammatory reactions, atherosclerosis, various degenerative neurological disorders as well as for delaying the natural process of the ageing of cells.

3 Claims, No Drawings

N-BENZOYL AMINO ACID DERIVATIVES PHARMACEUTICAL COMPOSITIONS CONTAINING THEM AND PROCESS FOR PREPARING SAME

This application is a continuation of application Ser. No. 08/085,003, filed Jun. 29, 1993.

This invention relates to novel N-benzoylamino acid derivatives of the general formula /I/,

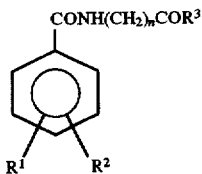

wherein $R^1$ and $R^2$, which are the same or different, stand for a hydroxyl group optionally bearing an acetyl group; or a $C_{1-6}$alkoxy group optionally substituted by a phenyl group;

$R^3$ represents: hydroxyl group; $C_{1-10}$alkoxy group; or a $C_{1-4}$alkoxy group optionally substituted by a phenoxy group optionally bearing a nitrogen-containing substituent; or an —$NR^4R^5$ group, where $R^4$ and $R^5$, which are the same or different, mean: hydrogen; hydroxyl group; $C_{1-12}$alkyl group; $C_{1-4}$alkyl group optionally substituted by a hydroxyl group or an amino group; or $R^4$ and $R^5$ together with the adjacent nitrogen form an optionally substituted 5- or 6-membered heterocyclic group optionally containing an additional nitrogen atom, this heterocyclic group optionally being substituted by an oxo group or an optionally phenyl-substituted $C_{1-4}$alkyl group or $C_{3-5}$alkenyl group; and when being piperazine, this heterocyclic group may be substituted also by a diaminopyrimidinyl or di(pyrrolidino)-pyrimidinyl group; and n means an integer from 2 to 15 with the proviso that:

when $R^3$ means hydroxyl group and n is 5, as well as one of $R^1$ and $R^2$ means a 4-hydroxyl group, then the other one of $R^1$ and $R^2$ is different from a 3-hydroxyl or 3-methoxy group; and when n is 2 or 3, then $R^1$ and $R^2$ cannot simultaneously stand for 2- and 3-methoxy group, as well as their tautomers, racemates and optically active individual (pure) isomers or mixtures thereof, the salts of these compounds and pharmaceutical preparations containing these compounds.

As an other aspect of the invention, a process is provided for the preparation of the new compounds of general formula (I).

The novel amino acid derivatives of general formula (I) according to the invention significantly inhibit the peroxidation of lipids and as a consequence, exert a number of valuable biological effects.

In a particularly preferred group of the compounds of general formula (I) each of $R^1$, $R^2$ and $R^3$ is hydroxyl group and n is 3, 4, 5 or 11.

In an other preferable group of the compounds of general formula (I) both $R^1$ and $R^2$ stand for hydroxyl group, $R^3$ means a $C_{1-10}$alkoxy group and n is 10 or 11.

A further advantageous group of the compounds of general formula (I) consists of substances, wherein both $R^1$ and $R^2$ mean hydroxyl and $R^3$ stands for a $C_{6-10}$alkylamino group or a piperazinyl group substituted by a 3-phenylpropyl or di(pyrrolidino)pyrimidinyl group.

The compounds of general formula (I) of the invention represent a substance class only less studied up to the present.

A few publications concerning this type of compounds are only found in the literature. Thus, A Bottazi et al. [Riv. Farm. Ter. 11, 215 (1971)] described the synthesis of 6-(3,4,5-trimethoxybenzoyl)aminohexanoic acid and analogues thereof containing carbon chains of various length. G. Razzaboni et al. [ibidem, 11, 221 (1971)] published the effect of these compounds against the heart-damaging effect of vasopressin. In these papers, 6-(4-hydroxy-3-methoxybenzoyl)aminohexanoic acid was also described but proved to be inactive in the test mentioned.

[(Dihydroxybenzoyl)aminomethyl]cyclohexanecarboxylic acids and 6-(dihydroxybenzoyl)aminocaproic acids inhibiting the platelet aggregation and migration of polynuclear leukocytes were described in the European patent specification No. 59, 108. Out of the (dihydroxybenzoyl)aminocaproic acids, 6-(3,4-dihydroxybenzoyl)aminocaproic acid has only been characterized without any data about its biological activity.

4-(2,3-Dimethoxybenzoyl)aminobutanoic acid was used as intermediate in the synthesis of polyamine-catecholamides [R. J. Bergeron et al.: J. Org. Chem. 46, 4524 (1981)].

Benzamides substituted by one, two or three hydroxyl group(s), were described in the published European patent application No. 0,353,753 to inhibit the glutamate receptor. Mono and dihydroxybenzamides with a related structure were published by S. A. Minasyan et al. [Arm. Khim. Zh. 39, 169 (1986)].

It is known that, due to their adverse (harmful) effects damaging the various organs of vital importance, free radicals contribute pathomechanism (pathogenesis) of many diseases, such as disorders accompanied with ischaemic reperfusion tissue injuries, degenerative neurological diseases, inflammatory processes or atherosclerosis [see e.g. C. Cross et al.: Ann. Intern. Med. 107, 526 (1987)].

It has been shown that primarily the phospholipids of the cellular membrane are damaged since changes accompanied by partial or total loss of function are induced in the membrane by the reactive lipid radicals formed by a radical initiator in the presence of metal ions.

Thus, recently a continuously increasing therapeutic demand has appeared for active agents capable to protect against the harmful (adverse) effects of free radicals. From this point of view compounds inhibiting the chain reaction of the lipid peroxidation process by trapping of the radicals and/or metal complex formation may be particularly valuable.

The best known natural antioxidant is vitamin E. Recently, a number of compounds with closely related structure have been published [see e.g. D. A. Janero et al.: Biochem. Pharm. 40, 551 (1990)]. Although these substances strongly inhibit the lipid peroxidation in vitro, their therapeutical use raised several problems: e.g. usually high doses of these compounds are effective under in vivo conditions and their acute use is limited.

Lipid peroxidation is strongly inhibited by a novel-type steroid derivative, the compound U74006F [J. M. Braughler et al.: J. Biol. Chem. 262, 10438 (1987)]. Although the in vivo activity of this substance has also been proven, its expected therapeutic use (mainly in the treatment of acute brain injuries) is a priori significantly limited by its weak absorption and relivatively rapid metabolism.

It has surprisingly been found during our investigations that the novel N-benzoylamino acid derivatives of general formula (I) of the invention inhibit the lipid peroxidation and, due to their favourable biological effects, they can advantageously be utilized in the indications mentioned above.

According to the invention the compounds of general formula (I) are prepared by:

a) reacting a benzoic acid of general formula (II),

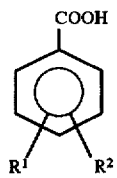

wherein
$R^1$ and $R^2$ are as defined above, or a derivative thereof suitable for acylating
with a compound of the general formula (III)

wherein
$R^3$ means hydroxyl group, $C_{1-10}$alkoxy group or a $C_{1-4}$alkoxy group optionally substituted by a phenoxy group optionally bearing a nitrogen-containing substituent, and n is as defined above, to obtain compounds of the general formula (I), wherein $R^3$ means hydroxyl group, $C_{1-10}$alkoxy group or a $C_{1-4}$alkoxy group optionally substituted by a phenoxy group optionally bearing a nitrogen-containing substituent and $R^1$, $R^2$ and n are as defined above; or b) reacting a compound of general formula (I) prepared according to the process a) above, wherein $R^3$ means hydroxyl group, and $R^1$, $R^2$ and n are as defined above, or a derivative thereof suitable for acylating, with a compound of the general formula $R^3H$, wherein $R^3$ means $C_{1-10}$alkoxy group or a $C_{1-4}$alkoxy group optionally substituted by a phenoxy group optionally bearing a nitrogen-containing substituent,
to obtain compounds of the general formula (I), wherein $R^3$ means $C_{1-10}$alkoxy group or a $C_{1-4}$alkoxy group optionally substituted by a phenoxy group optionally bearing a nitrogen-containing substituent, and $R^1$, $R^2$ and n are as defined above; or c) reacting a compound of general formula (I) obtained according to the process b) above, wherein $R^3$ stands for a methoxy or ethoxy group, and $R^1$, $R^2$ and n are as defined above, with an amine of the general formula $R^4R^5NH$;
to obtain compounds of the general formula (I), wherein $R^3$ means an $R^4R^5N$— group and $R^1$, $R^2$, $R^4$, $R^5$ and n are as defined above; or d) reacting a compound of the general formula (I) obtained according to the process a) above, wherein $R^3$ means hydroxyl group, and $R^1$, $R^2$ and n are as defined above, or a derivative thereof suitable for acylating, with an amine of the general formula $R^4R^5NH$, to obtain compounds of the general formula (I), wherein $R^3$ stands for an $R^4R^5N$— group, $R^1$ and $R^2$ are as defined above, except the hydroxyl groups and $R^4$, $R^5$ and n are as defined above; or e) hydrogenating a compound of the general formula (I) prepared according to any of the processes a)–d) above, wherein one of $R^1$ and $R^2$ is a benzyloxy group and the other one is as defined above or both $R^1$ and $R^2$ are benzyloxy groups, and $R^3$ and n are as defined above, to obtain compounds of the general formula (I), wherein one of $R^1$ and $R^2$ is hydroxyl group and the other one is as defined above, or both $R^1$ and $R^2$ represent hydroxyl groups, and $R^3$ and n are as defined above; or f) hydrogenating a compound of the general formula (I), prepared according to any of the processes c), d) or e) above, wherein $R^3$ stands for a 4-(3-phenyl-2-propenyl) piperazinyl group and $R^1$, $R^2$ and n are as defined above, to obtain compounds of the general formula (I), wherein $R^3$ means a 4-(3-phenylpropyl)piperazinyl group, $R^1$ and $R^2$ are as defined above, except benzyloxy group, and n is as defined above, and, if desired, removing (a) protective group(s) optionally being present in the $R^1$ and/or $R^2$ group(s) from the compound of general formula (I) obtained and, if desired, converting a compound of general formula (I) obtained to its salt and/or transforming a salt thereof to an other salt thereof and/or, if desired, liberating the free acid or base from a salt of a compound of the general formula (I).

According to the definition accepted in the literature [A. L. J. Beckwith: "Synthesis of Amides", in: "The Chemistry of Amides", Ed. J. Zabiczky, Interscience Publishers, London (1970)] the term "a derivative suitable for acylating" means an acid derivative being suitable for the N-acylation of amino compounds, e.g. for the synthesis of peptides usually under mild conditions. Acid derivatives of such type are e.g. acyl halides, first of all acyl chlorides and bromides, acid anhydrides, mixed anhydrides, e.g. the mixed anhydrides formed with ethyl chloroformate, as well as esters e.g. reactive esters and the methyl or ethyl esters.

In the carrying out of the processes according to the invention the mixed anhydride formed with ethyl chloroformate is a suitable acylating acid derivative in the case of acids of the general formula (I); whereas the acyl chloride is particularly useful in the case of acids of the general formula (II).

According to a preferred embodiment of process a) of the invention, the acyl chloride or anhydride of a compound of general formula (II) is reacted with an amino acid of the general formula (III) or with a derivative thereof. This reaction is carried out in water or in an organic solvent or in a mixture thereof in the presence of an acid binding agent at a temperature between 0° C. and 80° C. Suitable organic solvents are e.g. ethers such as dioxane or tetrahydrofuran or an aromatic hydrocarbon, e.g. benzene or toluene. An inorganic or organic base may be used as acid binding agent. When carrying out the reaction with an amino acid of general formula (III), it is suitable to work in a mixture of water and dioxane in the presence of sodium hydroxide as acid binding agent at a temperature between 20° C. and 40° C. When realizing the reaction with an amino acid ester of the general formula (III), it is suitable to work in benzene or toluene at a temperature between 50° C. and 80° C. in the presence of e.g. triethylamine as acid binding agent.

The progress and termination of the reaction can most simply be observed by using thin layer chromatography (TLC).

According to a preferable embodiment of process b) of the invention, an acid of the general formula (I) is reacted with an alcohol of the general formula $R^3H$ in an organic solvent, conveniently in an excess of the alcohol used at a temperature between 0° C. and the boiling point of the solvent in the presence of thionyl chloride of an acid catalyst to obtain compounds of the general formula (I), wherein $R^3$ means a lower alkoxy group. An inorganic of organic acid, e.g. hydrogen chloride or p-toluenesulfonic acid may be used as acid catalyst.

Alternatively, in order to obtain compounds of the general formula (I), wherein $R^3$ stands for a substituted alkoxy group and $R^1$ as well as $R^2$ are different from the hydroxyl group, the process b) of the invention is preferably carried out in such a way that an acid of the general formula (I) is reacted with an alcohol of the general formula $R^3H$-in an organic solvent, suitably in a halogenated hydrocarbon solvent, e.g. methylene chloride, in the presence of dicyclohexylcarbodiimide and optionally a catalyst at a temperature between 0° C. and 40° C. It is suitable to use a nucleophilic catalyst, e.g. 4-(N,N-dimethylamino)pyridine.

In order to obtain compounds of the general formula (I), wherein $R^3$ stands for an optionally substituted $C_{1-4}$alkoxy group and both $R^1$ and $R^2$ are different from hydroxyl group, the process b) of the invention is preferably performed in such a way that the acyl chloride prepared from the acid of general formula (I) is reacted with a compound of the general formula $R^3H$ in an organic solvent in the presence of an acid binding agent at a temperature between 0° C. and the boiling point of the solvent. Suitable solvents are aromatic hydrocarbons, e.g. benzene or toluene.

According to a preferred embodiment of process c) of the invention, the methyl or ethyl ester of an acid of the general formula (I) is reacted with an amine of the general formula $R^4R^5NH$ in an organic solvent, suitably in the excess of the amine used at a temperature between 50° C. and the boiling point of the solvent.

According to a preferable embodiment of process d) of the invention, an acid of the general formula (I) is reacted with an amine of the general formula $R^4R^5NH$ in an organic solvent in the presence of dicyclohexylcarbodiimide and optionally a nucleophilic catalyst at a temperature between 20° C. and 50° C.

According to an other preferred embodiment of the process d) of the invention, an acyl chloride or mixed anhydride, e.g. a mixed anhydride formed with ethyl chloroformate prepared from an acid of the general formula (I) is reacted with an amine of the general formula $R^4R^5NH$ in an organic solvent optionally in the presence of an acid binding agent at a temperature between 0° C. and 80° C.

In the process d) of the invention an aromatic hydrocarbon, e.g. toluene or benzene, halogenated hydrocarbon such as methylene chloride or an ether-type solvent, e.g. dioxane or tetrahydrofuran may preferably be used as solvents. An inorganic or organic base, e.g. potassium carbonate or triethylamine may be applied as acid binding agent.

According to a preferable embodiment of the process e) of the invention, a compound of the general formula (I) is hydrogenated in a Parr apparatus in an organic solvent in an acidic medium, suitably at a pH value between 3 and 5 in the presence of a palladium-on-carbon catalyst under atmospheric pressure. When $R^3$ is different from the hydroxy group, it is suitable to use an alcohol, e.g. ethanol as solvent; when $R^3$ stands for hydroxyl group, an ester such as ethyl acetate, or the mixture of water and an alcohol, or an aromatic hydrocarbon, e.g. benzene may be applied. The pH of the reaction mixture is suitably adjusted to the value desired by using an inorganic acid, e.g. hydrochloric acid.

Alternatively, the process e) of the invention may preferably carried out by performing the hydrogenation under the conditions of catalytic transfer hydrogenation. For this purpose, cyclohexene or ammonium formate are used as hydrogen sources, whereas the catalysts and solvents defined above are applied. This reaction is carried out at a temperature between 20° C. and the boiling point of the solvent, preferably at a temperature between 60° C. and 80° C.

According to a preferred embodiment of the process f) of the invention, the hydrogenation is carried out by using a palladium-on-carbon catalyst at room temperature under atmospheric pressure conveniently in ethanol at a pH value between 3 and 6.

The reaction mixture resulting from the processes described above can be worked up by methods commonly used in the practice of organic chemistry: e.g. by extraction, chromatography and/or crystallization following the removal of excess of the reactant and/or solvent optionally under reduced pressure. If desired, the compound of general formula (I) thus obtained may be purified e.g. by using chromatography and/or recrystallization or optionally converted to an acid addition salt which latter may be purified, if desired, by recrystallization following its separation.

It is obvious for one skilled in the art that the compounds used in the carrying out of process a) and b) have to be provided with protective group(s) in order to prevent side reactions. Such protective groups are well-known; from these, for the preparation of compounds according to the invention benzyl group and/or acetyl group are particularly useful, which can be removed in a known manner after carrying out the desired reaction(s), e.g. by hydrogenolysis in the case of benzyl group and by hydrolysis in the case of acetyl group.

Compounds of the general formula (I) according to the invention, which contain a sufficiently strong basic group, may be transformed to acid addition salts. This tranformation is carried out by dissolving the base in an appropriate solvent and portionwise adding the corresponding acid or a solution of this acid in a solvent under stirring. The product obtained is separated by filtration or crystallization after evaporating the solvent and, if desired, it is purified by recrystallization. An organic or inorganic acid, preferably a pharmaceutically acceptable acid such as hydrochloric acid, sulfuric acid, fumaric or tartaric acid may be used as acid components. An alcohol, ester, ether and/or ketone may be used as solvent. The salt formation is accomplished at a temperature between 0° C. and 80° C.: in the case of mineral acids preferably at 0°–20° C., in the case of organic acids preferably at 50°–80° C.

Compounds of the general formula (I) of the invention, wherein a free carboxyl group is present, can form a salt with a suitable cation. Cations of such type are suitably pharmaceutically acceptable inorganic or organic cations such as alkaline metal cations e.g. potassium or sodium cation, alkaline earth metal cations such as magnesium or calcium, or ammonium cation including e.g. the cations derived from an organic nitrogen-containing base, e.g. trialkylamine-derived cartons such as the triethylammonium ion. These salts are prepared e.g. by dissolving the acid in a suitable solvent and portionwise adding the corresponding base optionally as a solution in a solvent. Alcohols, esters, ethers and/or ketones may be used as solvents. The salt formation is carried out at a temperature between 0° C. and 80° C.

Benzoic acids of the general formula (II) or the derivatives thereof suitable for acylating in the embodiment of process a) of the invention are for the most part known in the literature. E.g. the various isomeric benzyloxy-hydroxybenzoic acids and their esters are known [see e.g.: J. Pharm. Soc. Jap. 72, 1081 (1952); Arch. Pharm. 293, 393 (1960)], furthermore the various isomeric acetoxyhydroxy-benzoic acids [see e.g.: Arch. Pharm. 292, 282 and ibidem 341 and 731 (1959); Liebigs Ann. Chem. 1984, 1230] as well as 2-acetoxy-3-methoxy- and 2,5-di(benzyloxy)benzoic acid and their acyl chlorides are also known [see: J. Pharm. Chim. 18, 247 (1933) and J. Org. Chem. 29, 2078 (1964), respectively]. Compounds of the general formula (II) not described till now can be prepared by using processes described in the literature or by analogous methods. For these an example will be given later in section "Preparation of Starting Substances".

The major part of the compounds of general formula (III) used in the process a) of the invention are known from the literature (see e.g.: T Wieland et al.: "Methoden zur Herstellung und Umwandlung yon Aminosäuren und Derivaten", in: Houben-Weyl, Methoden der Organischen Chemie, Vol. XI/2 page 269, Georg Thieme, Stuttgart 1958). The novel compounds can be prepared by using methods described in the literature or analogous processes.

The most part of the amines of general formula $R^4R^5NH$ applied as starting substances in the processes c) and d) of the invention are known from the literature: e.g. the derivatives of 1,2-ethanediamine and 1,3-propanediamine as well as the 1-substituted piperazines can be prepared as described in the literature [see e.g.: published European patent application No. 0.344,577; Belgian patent specification No. 523, 902; published PCT patent application No. 87/01706; as well as J. Med. Chem. 11, 804 /1968)]. The amines of general formula $R^4R^5H$ not yet described in the literature can be prepared by methods known from the literature or by using analogous processes.

As mentioned above, the compounds of general formula (I) of the invention possess valuable biological activities, e.g. lipid peroxidation-inhibiting effect as well as a protective action against ischaemic and/or reperfusion-induced tissue injuries and favorable central nervous system (CNS) effects. The lipid peroxidation-inhibiting effect of the compounds according to the invention was evaluated by the methods described hereinafter.

A) The effect of compounds of general formula (I) on the iron)II)-dependent peroxidation of arachidonic acid The peroxidation of arachidonic acid was measured by using the method of J. M. Braughler [J. Biol. Chem, 262, 10438 (1986)] at 37° C. in methanol. The compound to be tested was investigated at various concentrations. The peroxidation was initiated by adding $10^{-4}$ mol of iron(II) (ferrous) ion (to result in a final volume of 0.5 ml).

The thiobarbituric acid-reactive products were determined by a modification of J. A. Buege [Meth. Enzymology 52, 302 (1978)] as follows. 0.55 ml of 2% thiobarbituric acid was added to the solution and the samples were boiled for 20 minutes. After cooling down, the samples were diluted with distilled water, then chloroform was added. After centrifuging the tubes at 400× g for 7 minutes, the quantity of the thiobarbituric acid-reactive products was determined in the supernatant by spectrophotometry at 535 nm. The effect of the compound to be tested was characterized by its $IC_{50}$ value (i.e. the concentration resulting in an 50% inhibition). α-Tocopherol was used as reference compound. The results together with those of methods B) and C) are summarized in Table 1.

B) The effect of compounds of general formula (I) on the iron(II) ion-dependent peroxidation of brain homogenate The measurement was carried out by using the method of J. M. Braughler [J. Biol. Chem. 262, 10438 (1987)].

In these experiments OFA rats with a body-weight of 150–200 g were decapitated and brain homogenates were prepared in Krebs buffer solution, then the Method A) was followed.

C) The effect of compounds of general formula (I) on the NAOPH-dependent peroxidation of brain microsomes This study was carried out by using the method of T. J. Player and A. A. Morton [J. Neurochem. 37, 422 (1981)].

1) Microsome preparation

OFA rats of 3 months age were decapitated and their whole brain was homogenized in ice-cold 0.25M saccharose solution. After centrifuging the homogenate at 15000× g for 10 minutes, the supernatant was decanted and the residue was further centrifuged at 78000× g for 60 minutes. The preparation having a concentration of 10–20 mg of protein/ml was divided to aliquots.

2) Measurement of the microsomal lipid peroxidation

The measurement was carried out at 73° C. in a reaction mixture with the following composition; 0.05M Tris maleate (pH 6.8) buffer, 1.0 mM $KH_2SO_4$, 1.0 mM ADP, 0.2 nM $FeCl_3$ and 0.4 mM NADPH. NADPH was not added to the reaction mixture used for determination of the baseline activity. The reaction was initiated by adding 0.5 mg of membrane protein and stopped after incubation for 15 minutes. Subsequently, the samples were centrifuged at 950× g for 20 minutes. The thiobarbituric acid-reactive products were determined in 1 ml of supernatant each by using the method of Z. Dunied [Biochem. Pharmacol. 32, 2283 (1983)].

TABLE 1

Lipid peroxidation-inhibiting effect of compounds of the general formula (I)

| Compound (Example) No. | arachidonic acid substrate | $IC_{50}$[μmol/liter] on brain homogenate | brain microsome |
|---|---|---|---|
| 24 | 40 | 4.8 | 37 |
| 25 | 15 | 100 | 100 |
| 29 | 100 | 9 | 4.5 |
| 31 | 100 | 16 | 6.6 |
| 32 | 100 | 12 | 7.9 |
| 34 | 100 | 46 | 8.6 |
| 35 | 27 | 3.3 | 5.3 |
| 36 | 3.4 | 100 | 100 |
| 37 | 31 | 100 | 100 |
| α-Tocopherol | 1.5 | 7 | >100 |

It is obvious from the data of Table 1 that the lipid peroxidation-inhibiting effect of compounds tested of the invention is similar to or in several cases higher than of α-tocopherol used as reference compound.

The protective action of the compounds according to the invention against ischaemic and reperfusion-induced tissue injuries was evaluated by using the following iv vivo methods.

A) Effect of compounds of the general formula (I) on the ischaemic intestine injury in rats The method of D. A. Parks et al. [Surgery 92, 869 (1985)] was employed in these experiments.

Male CFY rats with an average body-weight of 250 g were starved for 24 hours before the surgical intervention but water was allowed ad libitum. The compound to be tested was orally administered in a 25 mg/kg dose by 2 hours before the operation.

The abdominal wall was opened along the median line under ether anaesthesia. The appropriate small intestine section was made ischaemic by ligating both small branches belonging to the pancreatico-duodenal artery. The shame-operated control animals were subjected only to the surgical intervention but their blood vessels were not ligated. The wound was closed and after 2 hours the abdominal cavity of the animals was again opened under ether anaesthesia. The thickened intestinal section was removed, its length and weight were determined and the significance was calculated by Duncan's test [D. B. Duncan: Biometrics 11, 1 (1955)] (with the weights corrected for a length of 20 mm) on the one hand, between the sham-operated and ischaemized vehicle-control animals; and on the other hand, between the ischaemized control animals and ischaemized animals treated with the compound to be tested. The edema-induced weight increase in the intestinal section was expressed as percentage. The results are summarized in Table 2.

TABLE 2

Effect of compounds of the general formula (I) on the ischaemized intestinal section in rats after oral administration of a 25 mg/kg dose

| Compound (Example) No. | Inhibition of ischaemia (%) |
|---|---|
| 24 | 63 |
| 25 | 61 |
| 29 | 52 |
| 30 | 70 |
| 35 | 63 |
| 36 | 76 |
| 37 | 73 |
| 40 | 72 |
| 41 | 75 |

Based on the above results, compounds of the invention tested possess a highly significant inhibitory effect against the adverse (harmful) sequels of ischaemia induced in the small intestine section.

B) Investigations on the model of reperfusion-induced arrhythmia in rats

In these experiments, the reperfusion-induced arrhythmia was developed in male SPRO rats weighing 400 g in average by using the method of D. Lamontagne et al. [Fundam. Clin. Pharmacol. 3, 671 (1989)].

The chest of artificially respirated animals was opened under pentobarbital anaesthesia and a thread was implanted under the left coronary. After an equilibration period of 15 minutes, in the case of an arterial blood pressure of at least 60 Hgmm, a myocardial ischaemia was induced by ligating the coronary for 5 minutes. This was followed by a reperfusion lasting for 10 minutes. The duration of arrhythmia, ventricular tachycardia (VT) and ventricular fibrillation (VF), respectively, developed within 3 minutes after reperfusion were registered in a lead-II ECG.

The average durations of VT and VF, respectively related to 1 minute were determined and the number of deaths induced by arrhythmia was also registered.

The compound to be tested was orally administered one hour before the experiment.

The statistical data were calculated by using Duncan's test (duration of VT and VF, respectively) or the $chi^2$ test (number of deaths) [S. Bolton in: "*Pharmaceutical Statistics*", pages 169–173 (1990), Marcel Dekkar] following the variance analysis in relation to the vehicle control.

The results are shown in Table 3.

TABLE 3

| Compound (Example) No. | Dose (mg/kg) p.o. | No. of cases N | Average duration of VT/VF S ± SE/min | No. of deaths (lethal VT/VF) |
|---|---|---|---|---|
| 25 | 100 | 10 | 28.0 ± 5.1** | 1/10* |
|  | 50 | 8 | 37.3 ± 5.7 | 4/8 |
| 36 | 100 | 8 | 20.6 ± 6.3** | 0/10* |
|  | 50 | 8 | 33.0 ± 9.9 | 4/8 |
| α-Tocopherol | 250 | 8 | 27.2 ± 7.1** | 1/8* |

TABLE 3-continued

| Compound (Example) No. | Dose (mg/kg) p.o. | No. of cases N | Average duration of VT/VF S ± SE/min | No. of deaths (lethal VT/VF) |
|---|---|---|---|---|
|  | 100 | 10 | 33.1 ± 7.1 | 4/8* |
| Vehicle control |  | 10 | 51.8 ± 3.1 | 9/10 |

*$p < 0.05$;
**$p < 0.01$

Based on the above results, both compounds of the invention showed a significant protective action against the reperfusion arrhythmia in a lower dose in comparison with α-tocopherol and considerably decreased the lethality.

C) Study on the neurotoxicity-inhibiting effect in mice

This study was carried out by using the method of R. E. Heikkila at al. [Science 224, 1451 (1984)] or by some modification of this method being very suitable to investigate compounds which are potentially active against Parkinson's disease.

The neurotoxic effect (dopamine depletion) was induced by 1-methyl-4-phenyl-1,2,5,6-tetrahydropyridine (hereinafter abbreviated: MPTP).

Male C-57 mice weighing 30 g in average were intraperitoneally treated with vehicle or with 100 mg/kg of the compound to be tested once daily for 3 successive days. One hour after the last administration, 40 mg/kg of MPTP and then an additional amount of 50 mg/kg of the compound to be tested were intraperitoneally administered. The animals were killed after 4 days, their brain was removed and the corpus striatum was separated. The dopamine level of corpus striatum was determined by high performance liquid chromatography (HPLC).

The results are shown in Table 4.

TABLE 4

| Compound (Example) No. | MPTP treatment | Dopamine level (μg/g tissue) | % of control |
|---|---|---|---|
| 36 | – | 20,67 ± 0,5 | 103 |
|  | + | 6,68 ± 1,0$^a$ | 33 |
| 24 | – | 20,44 ± 0,6 | 102 |
|  | + | 4,85 ± 1,7$^b$ | 24 |
| vehicle | – | 20,13 ± 0,6 | 100 |
|  | + | 1,74 ± 0,2 | 3 |

$^a p < 0.01$ in relation to the MPTP control
$^b p < 0.05$ in relation to the MPTP control Based on the results summarized in Table 4, the decrease in the dopamine level developed under the effect of MPTP was significantly moderated by the compounds of the invention.

On the basis of the pharmacological results, the compounds of general formula (I) according to the invention are expected to be useful for the treatment of diseases being in an indirect or direct connection with pathological oxidation processes occurring in the organism [B. Halliwell: Drugs 42, 570 (1991)]. Thus, these compounds can be particularly useful for the treatment and/or prevention of ischaemic and reperfusion tissue injuries, inflammatory reactions, atherosclerosis, various degenerative neurological disorders as well as for delaying the natural process of the ageing of cells.

The toxicity of the compounds according to the invention was studied in rats. The acute oral $LD_{50}$ values of all the compounds No. 24, 25, 29, 35, 36 and 37 were found to be higher than 1000 mg/kg, i.e. low.

The effectivity and low toxicity of the compounds of the invention together mean a valuable spectrum of activities and therapeutic safety.

For therapeutical use, the daily dose of compounds according to the invention is usually in the range from 1 mg/kg of body-weight to 10 mg/kg of body weight, preferably from 1 mg/kg of body weight to 5 mg/kg of body which is optionally administered in divided daily subdoses by considering the conditions of the adsorption.

For a therapeutical use, the active agents according to the invention are suitably transformed to pharmaceutical compositions by mixing them with nontoxic, inert, solid or liquid carriers and/or additives commonly used in the pharmaceutical practice, which are useful for enteral or parenteral administration. E.g. water, gelatine, lactose, starch, pectin, magnesium stearate, stearic acid, talc or vegetable oils may be used as carriers. As additives e.g. preservatives, wetting agents (surface active agents) as well as emulsifying and dispersing agents, buffers and flavours may be applied.

The active agents according to the invention can be transformed to the usual pharmaceutical compositions, e.g. solid forms (such as tablets, capsules, pills, suppositories) or liquid forms (such as aqueous or oily solutions, suspensions, emulsions, syrups as well as injectable solutions, suspensions and emulsion) by using the carriers and/or additives mentioned above.

The invention also relates to the pharmaceutical compositions containing a compound of the general formula (I) or a pharmaceutically acceptable salt thereof as active ingredient; as well as to a process for preparing these compositions.

The invention also relates to a method for treating diseases being in connection with pathological oxidation processess i.e. for the treatment and/or prevention of ischaemic and reperfusion tissue injuries, inflammations, atherosclerosis and various degenerative neurological disorders. This method comprises administering to the patient a therapeutically effective amount of an active ingredient of the formula (I) or pharmaceutically acceptable salt thereof.

The invention is illustrated in detail by the aid of the following non-limiting Examples. The melting points given in the Examples are uncorrected. Compounds having a melting point lower than room temperature were characterized by the retention value ($R_f$) obtained in thin layer chromatography.

Abbreviations: benzyl group is abbreviated by "Bz", ethyl group by "Et" and methyl group by "Me".

EXAMPLE 1

Preparation of 4-{N-[2,5-di(benzyloxy)benzoyl] amino-butyric acid 28.00 g (79.4 mmol) of 2,5-di(benzyloxy)benzoyl chloride were portionwise added to a sulution containing 17.32 g (168 mmol) of 4-aminobutyric acid in a mixture of 160 ml of water, 40 ml dioxane and 46 ml of 4M sodium hydroxide solution at 25°–28° C. during 90 minutes while stirring. After stirring the reaction mixture at 30° C. for 2.5 hours, 150 ml of water were added and the pH value of the solution was adjusted to 4 by adding 12M hydrochloric acid. The precipitate was filtered after cooling, washed with ice-cold water and dried to give 32.9 (99%) of the aimed product, m.p.: 135°–138° C.

By using the appropriate acyl chloride and amino acid as described above the compounds summarized in Table 5 were prepared.

TABLE 5

Compounds of the general formula (I), wherein $R^3$ means hydroxyl group

| Example No. | $R^1$ | $R^2$ | n | Yield % | M.p. °C. |
|---|---|---|---|---|---|
| 2 | 2-OBz | 5-OBz | 4 | 77 | 105–110 |
| 3 | 2-OBz | 5-OBz | 5 | 93 | 135–137 |
| 4 | 2-OBz | 5-OBz | 7 | 94 | 98–100 |
| 5 | 2-OBz | 5-OBz | 10 | 77 | 114–116 |
| 6 | 2-OBz | 5-OBz | 11 | 80 | 107–108 |
| 7 | 2-OBz | 5-OBu | 5 | 50 | 100–101 |

EXAMPLE 8

Preparation of ethyl 12-{N-[2,5-di(benzyloxy) benzoyl]amino}dodecanoate

To a solution of 4 g (7.5 mmol) of 12-{N-[2,5-di(benzyloxy)benzoyl]amino}dodecanoic acid (compound of Example 6) in 23 ml of anhydrous ethanol, 7.5 mmol of 20% ethanolic hydrogen chloride solution were added and the reaction mixture was stirred for 4.5 hours. After cooling the precipitate was filtered, washed with ether and dried to give 2.69 g (64%) of the aimed compound, m.p.: 70°–71° C.

The following compounds were prepared from the correspondig amino acid and alkanol containing hydrogen chloride as described above:

Ethyl 11-{N-[2,5-di(benzyloxy)-benzoyl] amino}undecanoate (compound of Example 9), yield 79%, m.p.: 50°–53° C.

Methyl 6-{N-[2,5-di(benzyloxy)benzoyl] amino}hexanoate (compound of Example 10), yield 87%, m.p.: 61°–63° C.

EXAMPLE 11

Preparation of 2-[4-(acetylamino)phenoxy]ethyl 4-{N-[2,5-di(benzyloxy) benzoyl]amino}butanoate 0.57 g (2.75 mmol) of dicyclohexylcarbodiimide was portionwise added to a solution of 1.05 g (2.5 mmol) of 4-{N-[2,5-di(benzyloxy)benzoyl]amino}butyric acid (compound of Example 1) in 16 ml of anhydrous methylene chloride at room temperature under stirring. After stirring the solution at the same temperature for 10 minutes 0.54 g (2.75 mmol) of 2-[4-(acetylamino)phenoxy]ethanol and 0.03 g (0.25 mmol) of 4-(N,N-dimethyl-amino)pyridine were added. The reaction mixture was stirred at room temperature for 4 hours, then diluted with methylene chloride and the solid product was filtered. The filtrate was successively washed with 5% acetic acid, 5% sodium hydrogen carbonate solution and water, then dried and evaporated under reduced pressure. The residue was separated by chromatography on a silica gel column by eluating with a 95:5 mixture of chloroform and methanol to obtain 0.82 g (55%) of the aimed product, m.p.: 141°–143° C.

EXAMPLE 12

Preparation of octyl 6-{N-[2,5-di(benzyloxy) benzoyl]amino}hexanoate

Step A) Preparation of 6-{N-[2,5-di(benzyloxy)benzoyl] amino}hexanoyl chloride 4.6 g (40 mmol) of thionyl chloride dissolved in 12 ml of anhydrous toluene were dropwise added to a suspension of 9.0 g (20 mmol) of 6-{N-[2,5-di(benzyloxy)benzoyl] amino}hexanoic acid (compound of Example 3) in 60 ml of anhydrous toluene and 0.93 g (13 mmol) of anhydrous dimethylformamide at room temperature during 5 minutes stirring. The reaction mixture was stirred at 50° C. for 1 hour then evaporated under reduced pressure to dryness at a temperature below 50° C. The residue obtained was thoroughly triturated with ether, filtered to obtain 7.68 g (82%) of the aimed product, m.p.: 90°–94° C.

Step B) Reaction of the acyl chloride with 1-octanol 0.66 g (5 mmol) of 1-octanol was dropwise added to the solution of 1.5 g (3.2 mmol) of 6-{N-[2,5-di(benzyloxy) benzoyl]amino}hexanoyl chloride in 15 ml of anhydrous acetonitrile and 0.29 g (3.7 mmol) of anhydrous pyridine during 5 minutes under cooling and stirring at 0°–5° C. The reaction mixture was stirred at room temperature for 10 hours, then evaporated under reduced pressure to dryness at a temperature below 50° C. The residue obtained was dissolved in 40 ml of ether and was successively washed with water, 2% sodium hydroxide solution and finally with water, then dried and evaporated under reduced pressure. The residue was purified on a silicagel column by using ethyl acetate as eluent to give 0.96 g (54%) of the aimed compound, m.p.: 48°–50° C.

EXAMPLE 13

Preparation of N-(2-hydroxyethyl)-{6-{N-[2,5-di (benzyloxy)benzoyl] amino}hexanoic acid amide}

A solution containing 1.60 g (3.5 mmol) of methyl 6-{N-[2,5-di(benzyloxy)benzoyl]amino}hexanoate (compound of Example 10) in 4.9 g (70 mmol) of 2-aminoethanol was reacted under nitrogen at 100° C. for 2 hours while stirring. After cooling down, the reaction mixture was diluted with 70 ml of chloroform and acidified to pH 3 by adding 5M hydrochloric acid. After separation the aqeuous phase was extracted twice with chloroform, the combined organic phase was washed with water, dried and evaporated under reduced pressure. The residue was washed with ether and recrystallized from ethyl acetate to give 1.1 g (63%) of the aimed compound, m.p.: 103°–104° C.

The following compounds were similarly prepared by carrying out the reaction with the corresponding amine at the boiling point of the amine:

N-(2-Aminoethyl)-{6-{N-[2,5-di(benzyloxy)benzoyl] amino}hexanoic acid amide} (compound of Example 14), yield 43%, m.p.: 88°–89° C.

N-Octyl-{6-{N-[2,5-di(benzyloxy)benzoyl] amino}hexanoic acid amide} (compound of Example 15), yield 47%, m.p.: 111°–112° C.

By carrying out the above reaction with a solution of methylamine in ethanol at room temperature N-methyl-{4-{N-[2,5-di(benzyloxy)benzoyl] amino}butanoic acid amide} (compound of Example 18), was obtained in a yield of 88%, m.p.: 135°–137° C.

EXAMPLE 17

Preparation of 5-{N-[2,5-di(benzyloxy)benzoyl] amino}pentylcarbohydroxamic acid

Step A) Preparation of 6-{N-[2,5-di(benzyloxy)benzoyl] amino} hexanoyl chloride 0.36 g (5 mmol) of anhydrous dimethylformamide and 35 ml of anhydrous methylene chloride were added to 2.23 g (5 mmol) of 6-{N-[2,5-di(benzyloxy)benzoyl]amino}caproic acid (compound of Example 3). To the solution obtained 1.43 g (11.25 mmol) of oxalyl chloride were portionwise added at 0° C. under stirring, then the reaction mixture was stirred at the same temperature for 40 minutes. The solution thus obtained was used in the following step B).

Step B)

The solution of the acyl chloride obtained in the preceding Step A) was added in four portions to a solution of 1.4 g (20 mmol) of hydroxylamine hydrochloride and 3.0 g (30 mmol) of triethylamine in 17.5 ml of tetrahydrofuran and 1.75 ml of water during 10 minutes at 0° C. under stirring. After stirring the reaction mixture at 20° C. for 90 minutes, 60 ml of 2N hydrochloric acid were added, the phases were separated and the aqueous phase was extracted twice with methylene chloride.

The organic phase was washed with water, dried and evaporated under reduced pressure at a temperature below 40° C. The residue was purified on a silica gel column by using a 9:1 mixture of ethyl acetate with methanol as eluent to give the aimed compound in a yield of 16%, m.p.: 61°–63° C.

The compound of Example 18 was obtained by using pyrrolidone sodium salt in dimethylformamide at 40° C.

1-{6-{N-[2,5-di(benzyloxy)benzoyl]amino}hexanoyl}-5 (1H)-pyrrolidone (compound of Example 18), yield 27%, m.p.: 94°–95° C.

EXAMPLE 19

Preparation of 1-{6-{N-[2,5-di(benzyloxy)benzoyl] amino}hexanoyl}-4-methyl-piperazine Step A) Preparation of mixed anhydride 0.24 g (2.2 mmol) of ethyl chloroformate was added to a solution of 1 g (2.2 mmol) 6-{N-[2,5-di(benzyloxy)benzoyl] amino}hexanoic acid (compound Example 3) in 4.5 ml of anhydrous methylene chloride and 0.22 g (2.2 mmol) of triethylamine at 0° C. under stirring. After stirring the reaction mixture at 0° C. for 30 minutes 5 ml of ice-water were added, the phases were separated, the organic phase was dried over anhydrous magnesium sulfate, then concentrated to a volume of 2 ml under reduced pressure at 25° C. The residual liquid was used in this form in the next step without delay.

Step B)

The mixed anhydride prepared in the preceding step A) was poured to the solution of 0.22 g (2.2 mmol) of methyl-piperazine in 2.2 ml of anhydrous tetrahydrofuran at 0° C., then the reaction mixture was stirred at 0° C. for 1 hour. After pouring the mixture into 5 ml of ice-water, tetrahydrofuran was distilled off under reduced pressure and the aqueous phase was extracted with chloroform. The organic phase was washed with water, dried and the solution was evaporated under reduced pressure. The residue was purified by chromatography on a silicagel column by using a 10:1 mixture of chloroform and methanol as eluent to obtain 0.91 g (78%) of the aimed compound, m.p.: 78°–79° C.

The compounds summarized in Table 6 were prepared as described above, i.e. by preparing the mixed anhydride from the corresponding acid according to step A) and by reacting the mixed anhydride with the corresponding amine according to the step B).

TABLE 6

Compounds of the general formula (I), wherein $R^1$ means 2-benzyloxy group, $R^2$ stands for 5-benzyloxy group

| Example No. | $R^3$ | n | Yield % | M.p. °C. or $R_f$ value |
|---|---|---|---|---|
| 20 | [piperazine]–N–CH$_2$–CH=CH–[phenyl] | 5 | 72 | 0.5* |
| 21 | [complex bis-piperazine structure] | 5 | 55 | 139–141 |

*chloroform/methanol = 24:1 was used as eluent

EXAMPLE 22

Preparation of 8-[N-(2,5-dihydroxybenzoyl)amino]octanoic acid 1.85 g (22.5 mmol) of cyclohexene, 0.5 g of 10% palladium-on-carbon catalyst and 0.15 g of hydroquinone were added to a solution of 1.2 g (2.5 mmol) of 8-{N-[2,5-di(benzyloxy)benzoyl]amino}octanoic acid (compound of Example 4) in 18 ml of anhydrous ethanol under nitrogen. After boiling under reflux for 1 hour while stirring, the reaction mixture was cooled down, diluted with 12 ml of water, the catalyst was filtered off under nitrogen and washed with a 9:1 mixture of ethanol and water. After evaporating the solvent under reduced pressure, the residue was thoroughly triturated with 10 ml of water and then stirred at 0° C. for 1 hour.

The crystalline product was filtered, washed with ice-water and dried to give 0.35 g (46%) of the aimed compound, m.p.: 150°–151° C.

The compounds listed in Table 7 were prepared as described above by using the corresponding starting substances. (In the cases of compounds of Examples 23 and 27 a sixty-fold amount of cyclohexene was used.)

TABLE 7

Compounds of the general formula (I)

| Example No. | $R^1$ | $R^2$ | $R^3$ | n | Yield % | M.p. °C. |
|---|---|---|---|---|---|---|
| 23 | 2-OH | 5-OH | OH | 10 | 47 | 136–138 |
| 24 | 2-OH | 5-OH | OH | 11 | 74 | 142–143 |
| 25 | 2-OH | 5-OH | OH | 5 | 74 | 126–127* |
| 26 | 2-OH | 5-OBu | OH | 5 | 68 | 95–96 |
| 27 | 2-OH | 5-OH | O–(CH$_2$)$_2$–O–[phenyl]–NHAC | 3 | 72 | 140–141 |
| 28 | 2-OH | 5-OH | NH–CH$_2$–CH$_2$–NH$_2$ | 5 | 87 | 113–115 (dihydrochloride) |
| 29 | 2-OH | 5-OH | NH–(CH$_2$)$_7$–CH$_3$ | 5 | 50 | 101–102 |
| 30 | 2-OH | 5-OH | –N[pyrrolidinone] | 5 | 61 | 130–131 |

*After recrystallization from aqueous hydrochloric acid (pH = 3) m.p.: 142–144° C. (crystal dimorphism).

EXAMPLE 31

Preparation of ethyl 11-[N-(2,5-dihydroxybenzoyl)amino]undecanoate

A solution containing 3.55 g (6.5 mmol) of ethyl 11-{N-[2,5-di(benzoyloxy)benzoyl]amino}undecanoate (compound of Example 9) in 95 ml of ethanol was adjusted to a pH value of 3 by adding concentrated hydrochloric acid, and hydrogenated in the presence of 1.3 g of 10% palladium-on-carbon catalyst under environmental pressure. After filtering off the catalyst, the solution was evaporated under reduced pressure, the residue was thoroughly triturated with 10 ml petroleum ether and dried to obtain 1.60 g (67.3%) of the aimed compound, m.p.: 72°–74° C.

The compounds listed in Table 8 were prepared as described above by using the corresponding di(benzyloxy) benzoylamino acid derivatives as starting substances. The compound of Example 34 was obtained from the corresponding 4-(3-phenyl-2-propenyl)piperazinyl derivative (compound of Example 20).

The compounds summarized in Table 10 were prepared as described in step A) and step B) above, respectively, from the corresponding dihydroxybenzoic acid and amino acid as starting substances.

TABLE 8

Compounds of the general formula (I), wherein $R^1$ stands for 2-hydroxyl group, and $R^2$ represents an 5-hydroxyl group

| Example No. | $R^3$ | n | Yield % | M.p. °C. or $R_f$ value |
|---|---|---|---|---|
| 32 | OEt | 11 | 60 | 94–95 |
| 33 | 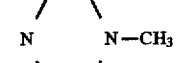 | 5 | 75 | 134–137 (dihydrochloride) |
| 34 | 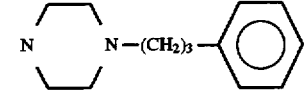 | 5 | 95 | 0.4ª (hydrochloride dihydrate) |
| 35 | 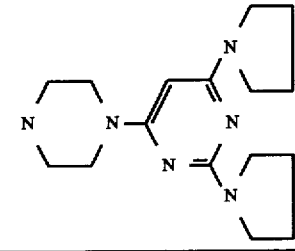 | 5 | 32 | 218–223 |

ªethyl acetate/methanol/ammonium hydroxide = 9:1:0.5 was used as eluent;

EXAMPLE 36

Preparation of 4-[N-(2,5-dihydroxybenzoyl)amino] butyric acid

Step A) Preparation of the acylating component

To a suspension containing 7.52 g (49 mmol) of 2,5-dihydroxybenzoic acid in 50 ml of anhydrous toluene, 0.1 mol of anhydrous pyridine was added, then 7.18 g (60 mmol) of thionyl chloride were dropped to the solution while cooling at 10° C. under stirring. Subsequently, the reaction mixture was stirred at 60° C. for 6 hours, then the solution was decanted from the undissolved oil. The solution was evaporated at a temperature below 30° C. under reduced pressure and then evaporated to constant weight by a pump under a pressure of 1 Torr. The yellow foam obtained was immediately used in the next step. The product was obtained in a yield of 6.7 g, m.p.: 55°–58° C.

Step B) Acylation of the amino acid 4.33 g (42 mmol) of 4-aminobutyric acid were dissolved in a mixture containing 34 ml of water, 10 ml of dioxane and 11.5 ml (46 mmol) of 4M sodium hydroxide solution and reacted with the acylating component obtained in the preceding step A) as described in Example 1 to give 2.4 g (42%) ot the aimed compound, m.p.: 152°–156° C.

TABLE 9

Compounds of the general formula (I)

| Example No. | $R^1$ | $R^2$ | $R^3$ | n | Yield % | M.p. °C. |
|---|---|---|---|---|---|---|
| 37 | 2-OH | 5-OH | OH | 4 | 28 | 144–146 |
| 38 | 2-OH | 3-OH | OH | 5 | 50 | 58–64 |
| 39 | 3-OH | 4-OH | OH | 3 | 53 | 159–163 |

EXAMPLE 40

Preparation of methyl 4-[N-(2,5-dihydroxybenzoyl) amino]butanoate

After dropwise adding 8.5 g (71 mmol) of thionyl chloride to 30 ml of anhydrous methanol at 10° C. during 30 minutes under cooling by ice while stirring, the solution was stirred at the same temperature for additional 45 minutes, then 5.1 g (20 mmol) of 4-[N-(2,5-dihydroxybenzoyl)amino]butyric acid (compound of Example 36) were portionwise added. The reaction mixture was allowed to warm to room temperature and stirred at 80° C. for 8 hours. After filtering the precipitate by suction and washing with methanol 3.7 g (68%) of the aimed compound were obtained, m.p.: 155°–159° C.

The following compound was prepared as described above by using the corresponding amino acid:

Methyl 6-{[N-(2,5-dihydroxybenzoyl)amino]hexanoate} (compound of Example 41), yield 73%, m.p.: 100°–103° C.

EXAMPLE 42

Preparation of methyl 6-[N-(2-hydroxy-3-methoxybenzoyl)amino]hexanoate 2.3 g (10 mmol) of 2-acetoxy-3-methoxybenzoyl chloride dissolved in 18 ml of anhydrous benzene were dropwise added to the suspension of 1.80 g (10 mmol) methyl 6-aminohexanoate hydrochloride in 2.2 g (22 mmol) of anhydrous triethylamine and 18 ml of anhydrous benzene under nitrogen at room temperature while stirring. After boiling under reflux for 2 hours while stirring, the reaction mixture was cooled down, the precipitate was filtered by suction and the filtrate was evaporated 20 ml of water were portionwise added to the residue, the solution was extracted with ethyl acetate, the organic phase was washed with 1M hydrochloric acid and water, then dried. The solvent was evaporated under reduced pressure. The residue was purified by chromatography on a silica gel column by using a 3:4 mixture of petroleum ether and ethyl acetate to obtain 1.62 g (55%) of the title compound, m.p.: 69°–70° C.

Preparation of the novel starting substances is illustrated by the following Example.

The novel benzoic acid derivatives of the general formula (II) can obtained e.g. as follows.

Preparation of 2-benzyloxy-5-butoxybenzoic acid

A suspension containing 1.9 g (9 mmol) of 5-butoxy-2-hydroxybenzoic acid, 3.85 g (30 mmol) of benzyl chloride and 5 g (36 mmol) of anhydrous potassium carbonate in 18 ml of anhydrous ethanol was boiled under reflux for 20 hours while stirring. The reaction mixture was cooled to room temperature and after adding 20 ml of water and thoroughly shaking, the three phases formed were separated. The medium phase was boiled under reflux with 1.1 g (27.5 mmol) of sodium hydroxide dissolved in 7 ml of ethanol and 5 ml of water for 2.5 hours under stirring. After cooling down the solution was mixed with 15 ml of water under cooling by ice, the pH value of the mixture was adjusted to 4 by adding 5M hydrochloric acid and stirred for 1 hour. After extracting the product with ethyl acetate and drying, the solution was evaporated to dryness under reduced pressure to give 1.5 g (55%) ot the aimed product, m.p.: 79°–82° C.

We claim:

1. An N-Benzoylamino acid compound of the formula (I),

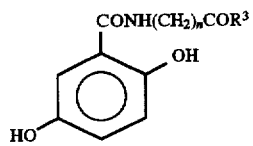

or a pharmaceutically acceptable salt thereof
wherein $R^3$ is selected from the group consisting of a hydroxyl group and a $C_1$–$C_{10}$ alkoxy group; and n is an integer from 10 to 15.

2. A pharmaceutical composition for the treatment of patients suffering from disorders being in an indirect or direct connection with pathological oxidation process occuring in an organism, which comprises a therapeutically effective amount of a compound as defined in claim 1, or a pharmaceutically acceptable salt thereof, in a pharmaceutically acceptable carrier.

3. A pharmaceutical composition according to claim 2 wherein the disorders are ischaemic and reperfusion injuries, inflammations, atherosclerosis, or degenerative neurological disorders.

* * * * *

UNITED STATES PATENT AND TRADEMARK OFFICE
CERTIFICATE OF CORRECTION

PATENT NO. : 5,705,529
DATED : JANUARY 6, 1998
INVENTOR(S) : MATYUS, ET AL

It is certified that error appears in the above-identified patent and that said Letters Patent is hereby corrected as shown below:

COVER PAGE, LEFT COLUMN, ITEM [73] should read as follows:

--[73] ASSIGNEE: NISSHIN FLOUR MILLING CO., LTD., TOKYO, JAPAN

Signed and Sealed this

Third Day of November, 1998

BRUCE LEHMAN

Attest:

Attesting Officer

Commissioner of Patents and Trademarks